United States Patent [19]
Darr et al.

[11] Patent Number: 5,140,043
[45] Date of Patent: Aug. 18, 1992

[54] STABLE ASCORBIC ACID COMPOSITIONS

[75] Inventors: Douglas Darr, Timberlake; Sheldon R. Pinnell, Durham, both of N.C.

[73] Assignee: Duke University, Durham, N.C.

[21] Appl. No.: 339,488

[22] Filed: Apr. 17, 1989

[51] Int. Cl.$^5$ .............................................. A61K 31/34
[52] U.S. Cl. ...................................................... 514/474
[58] Field of Search ........................................ 514/474

[56] References Cited

U.S. PATENT DOCUMENTS

| | | | |
|---|---|---|---|
| 2,132,662 | 11/1938 | Volwiler et al. | 260/501 |
| 2,134,246 | 10/1938 | Basel et al. | 23/250 |
| 2,140,989 | 12/1938 | Eisenbrand et al. | 260/284 |
| 2,150,140 | 3/1939 | Warnat | 260/344 |
| 2,161,651 | 6/1939 | Roberts | 334/58 |
| 2,165,184 | 7/1939 | Pasternack et al. | 514/474 |
| 2,187,467 | 1/1940 | Stuart | 514/474 |
| 2,249,903 | 1/1941 | Lautenschlager et al. | 514/474 |
| 2,294,937 | 9/1942 | Ruskin | 260/344 |
| 2,297,212 | 9/1942 | Gockel | 514/474 |
| 2,400,171 | 11/1945 | Ruskin | 514/474 |
| 2,442,461 | 2/1945 | Karrer et al. | 514/474 |
| 2,585,580 | 6/1948 | Opplt | 514/474 |
| 2,721,161 | 10/1955 | Maiese | 514/474 |
| 4,199,469 | 4/1980 | Walzer | 252/146 |
| 4,294,852 | 10/1981 | Wildnauer et al. | 424/317 |
| 4,367,157 | 1/1983 | Sherman | 252/106 |
| 4,372,874 | 2/1983 | Modrovich | 436/176 |
| 4,722,936 | 2/1988 | Jacob | 514/474 |
| 4,818,521 | 4/1989 | Tamabuchi | 514/474 |
| 4,847,071 | 7/1989 | Bissett et al. | 424/59 |
| 4,938,969 | 7/1990 | Schinitsky et al. | 424/642 |
| 4,946,671 | 8/1990 | Bissett et al. | 424/59 |
| 4,954,332 | 9/1990 | Bissett et al. | 424/59 |
| 4,983,382 | 1/1991 | Wilmott et al. | 424/62 |

FOREIGN PATENT DOCUMENTS 63-37087 8/1989 Japan.

OTHER PUBLICATIONS

Chemical Abstracts, 110:198950r, (1989), (Pub. Nov. 1988).

Lewin, Sherry, *Vitamin C: Its Molecular Biology and Medical Potential*, Academic Press, 1976, pp. 4-222.

E. Meucci et al., *Ascorbic Acid Stability in Aqueous Solutions*, Acta Vitaminol. Enzymol., 1985, 7(3-4), 147-154.

Ciminera, J. et al., *Stable Ascorbic Solution for Parenteral Use*, Journal of the American Pharmaceutical Association, (1946), pp. 363-365.

H. Schaefer et al., *Skin Permeability*, Springer-Velag, 1982, pp. 739-740.

Karl-Josef Kunert et al., *The Effect of Vitamin C on in vivo Lipid Peroxidation in Guinea Pigs as Measured by Pentane and Ethane Production*, Lipids, vol. 18, No. 4, (1983), pp. 271-274.

Takashima et al., *Ascorbic Acid Esters and Skin Pigmentation*, American Perfumer and Cosmetics, vol. 86, No. 7, Jul. 1971.

Sasha Englard et al., *The Biochemical Functions of Ascorbic Acid*, Annual Reviews Inc., 1986, pp. 365-406.

Imai, Yoshio et al., *The Antiscorbutic Activity of L-Ascorbic Acid Phosphate Given Orally and Percutaneously in Guinea Pigs*, The Japanese Journal of Pharmacology, vol. 17, No. 2, Jun. 1967, pp. 317-324.

Ascorbic Acid, Merck Service Bulletin, 1941.

*Primary Examiner*—Leonard Schenkman
*Attorney, Agent, or Firm*—Cushman, Darby & Cushman

[57] ABSTRACT

Stable topical aqueous compositions are provided containing a concentration of L-ascorbic acid above about 1% (W/V) and maintaining a pH below about 3.5.

42 Claims, 8 Drawing Sheets

STABLE ASCORBIC ACID COMPOSITIONS

The present invention relates to stable topical compositions which contain L-ascorbic acid and which prevent ultraviolet damage to skin. More particularly, it relates to topical compositions containing L-ascorbic acid (vitamin C) which are stabilized in aqueous solutions by providing a concentration of L-ascorbic acid above about 1% (w/v) and maintaining the pH below about 3.5.

Considerable effort has been expended to find ways to prevent adverse changes in the skin brought about by ultraviolet (UV) exposure. Preventative approaches include physically blocking or absorbing the UV radiation before it can enter the skin. This technique is effective but is cumbersome because these prior art sunblockers or absorbers usually must be applied before every exposure and can be washed off with water. Thus, for example, after every swim they must be reapplied. Further, the long-term side effects of many of these prior art compositions are not known.

L-ascorbic acid has many known biological functions from enzymatic co-factor to "sparing" agent against vitamin E depletion. See, for example, England and Seifter, "The Biochemical Functions of Ascorbic Acid," Ann. Rev. Nutri. 6: 365-406, (1986); Kunert and Tappel, "The Effect of Vitamin C on in vivo Lipid Peroxidation in Guinea Pigs as Measured by Pentane and Ethane Production, Lipids 18: 271-74 (1983). The latter function may partly account for its "anti-oxidant" status. Additionally, at higher concentrations, ascorbic acid is known to react with both the superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, break down DNA, inactivate enzymes and so forth. An immense amount of work has been done in the last two decades documenting the deleterious behavior of oxygen radicals. Several recent texts on the subject include:

*Oxy-radicals in Molecular Biology & Pathology*, D Cerutti, I. Fridovich, J. McCord, eds., (Alan R. Liss, Inc. New York, 1988);

*Biological Role of Reactive Oxygen Species in Skin*, O. Hayaishi, S. Inamura, Y. Mayachi, eds. (Elsevier Press, New York, 1987);

*Free Radicals, Aging and Decenerative Diseases*, J. E. Johnson, Jr., R. Walford, D. Harmon, J. Miguel, eds. (Alan Liss, Inc., New York, 1986);

*Free Radicals in Biology and Medicine*, B. Halliwell and J. M. C. Gutteridge, eds. (Clarendon Press, Oxford, 1985); and

*Oxidative Stress* Helmut Sies, ed. (Academic Press, 1985).

Also addressing the subject are several symposia, including "Oxygen Radicals and Tissue Injury" Proceedings from an Upjohn Symposium (April, 1987); and "Oxygen Free Radicals", Proceedings from National Heart, Lung & Blood Institute (National Institute of Health, Washington, D.C., Dec. 1987).

Ascorbic acid has been shown to stimulate collagen synthesis in vitro which may provide better understanding of pathologies related to diminished collagen production in vivo. See for example, S. R. Pinnell, "Regulation of Collagen Biosynthesis by Ascorbic Acid: A Review", Yale J. Biol. Med. 58: 554-59 (1985).

L-Ascorbic acid (or vitamin C), which has a long and illustrious history, is chemically defined as an $\alpha$-ketolactone with the following structure:

The number 2 and 3 carbons are double-bonded and contain an acid-ionizable hydrogen in water (pK $=4.2$). Ascorbic acid is also a moderately strong reductant. These properties, which lead to instability in the ascorbic acid structure, are well known and have been burdensome to pharmacologists when attempting to formulate active ascorbic acid solutions. Thus, at higher pH's, the ascorbic acid increasingly becomes the notoriously unstable ascorbate anion. This instability may be due to several causes not restricted to:

1. a) Stereochemical strain due to polar repulsive forces. Thus, when the 2-hydroxy group is the one to ionize, it places two negative charges (the other being on the carboxyl oxygen) in close proximity which favors ring disruption.

b) Oxidative degradation due to the ascorbate anion's propensity to act as a reductant. The one-electron oxidation product (dehydroascorbate free radical) tends to disproportionate, forming another ascorbate molecule and the two-electron oxidation product, dehydroascorbate, which is extremely unstable in aqueous solutions and breaks down to ultimately form species such as L-threonic acid and oxalic acid. Transition metal ions can catalyze these reactions.

c) Degradation due to bulk water attack. Thus at lower ascorbate concentrations or ionic strength, water itself can react with and degrade the ascorbate molecule. For details of the above mentioned reactions, see *Vitamin C: Its Molecular Biology and Medical Potential*, Sherry Lewin, ed. (Academic Press, London, 1976).

For these reasons, among others, scientists working in the field have had difficulty in formulating stable solutions of ascorbic acid which would be useful for cosmetic, dermatologic, or ophthalmic needs. Nevertheless, because of the many beneficial pharmaceutical effects attributed to ascorbic acid, numerous attempts have been made to overcome these difficulties.

Thus, the literature describes ascorbic acid compositions formed by using a very low weight percent ascorbic acid, or a nonaqueous solvent, or by using derivatives of ascorbic acid, usually in a solution buffered to a pH above 4.0. See, for example, Takashima et al, "Ascorbic Acid Esters and Skin Pigmentation," Am. Perfumer & Cosmetics 86: 29 (July 1971) (esterifying the hydroxyl group to form ascorbic acid-3-phosphate and maintaining an alkaline pH); Ciminera and Wilcox, "Stable Ascorbic Acid Solution for Parenteral Use", J. Am. Pharm. Assoc. Sci. Ed. 35: 363 (1946) (buffering an aqueous solution with an alkaline sodium salt). See also U.S. Pat. No. 4,367,157 which discloses stabilizing an aqueous ascorbic acid solution by adding monothioglycerol and maintaining the pH between 4 and 7; U.S. Pat. No. 2,400,171 which discloses stabilizing ascorbic acid by converting it to its calcium or zinc salt and preferably maintaining the pH at 7 to 7.3; U.S. Pat. No. 2,442,461 which discloses stabilizing calcium ascorbate by adding an aliphatic thiocarboxylic acid and maintaining the pH between 5.2 and 5.6; U.S. Pat. No. 2,585,580 which discloses stabilizing ascorbic acid with thio-sugars and maintaining the pH between 4.0 and 6.5; and U.S. Pat. No. 4,372,874 which discloses actually removing the water to below 0.5 wt.% by using a desiccant. In many cases, these techniques have been successful in obtaining stable solutions but have been reasonably expensive and have yielded a product with less desirable properties than ascorbic acid in its unmodified form.

We have now discovered a new, more economical, stable topical composition which consists essentially of at least about 1 wt.% L-ascorbic acid, preferably from about 3 to 20 wt.% L-ascorbic acid, and more preferably about 5 to 10 wt.% L-ascorbic acid in water and a carrier for topical application. Any composition containing at least about 1 wt.% L-ascorbic acid is expected to have beneficial effects, with the concentration of L-ascorbic acid being primarily limited by its solubility in the water/carrier system. The ratio of water to carrier is at least 1:1, and more preferably from 2:1 to 10:1, and the pH of the composition is no more than about 3 to 3.5, preferably no more that about 2.5. Such a composition appears to allow ready penetration into the skin and retards the damage caused by ultraviolet light.

Carriers for topical application useful in practicing the invention include, but are not limited to, alkylene glycols, or alkylene glycols in combination with one or more derivatives of hydroxyalkylcellulose. In one embodiment, the alkylene glycol is propylene glycol and the hydroxyalkylcellulose is hydroxypropylcellulose. When a combination of alkylene glycol and hydroxyalkylcellulose is used, a useful ratio of alkylene glycol to hydroxyalkylcellulose is from about 30:1 to 5:1 and a particularly useful ratio is 30:. Without limitation, other carriers known to those skilled in the art which are compatible with water and are biologically acceptable are expected to provide equivalent compositions within the scope of this invention. For example, alcohols such as ethanol and propanol, glycols such as butylene or hexylene glycol, and polyols such as sorbitol may be employed. Alternatively, polyethylene or polypropylene glycols, mineral oil or glycerol can be used. Also contemplated by this invention are biologically acceptable hydroxyalkylcelluloses.

As one skilled in the art would recognize, the ascorbic acid may be provided by the addition of any reducing analog of ascorbic acid, such as D-isoascorbic acid or perhaps by the addition of other small reducing compounds such as, but not limited to, glutathione, L-cysteamine, etc. Such forms would be expected to provide an equivalent composition to that claimed and are within the scope of the invention.

The water used is preferably distilled and/or deionized, but any water may be used which does not contain contaminants which would affect the stability of the ascorbic acid composition. The effects of water of varying purity on ascorbic acid stability is discussed in Meucci et al., "Ascorbic Acid Stability in Aqueous Solutions," Acta Vitaminol. Enzymol. 7(3-4): 147-54 (1985), incorporated herein by reference.

A metal chelator, such as diethylene triaminepentaacetic acid (DTPA) or ethylenediamine-di(o-hydroxyphenylacetic acid) (EDDHA), can be added to the composition in minor amounts (.001% to 0.1% (w/v)) to provide additional stability to the ascorbic acid, particularly when used at the lower concentration.

The required pH of the composition ensures that greater than 82% of the ascorbic acid remains in the protonated, uncharged form. Although not wishing to be bound by theory, we believe that the protonated form of ascorbic acid used in our invention is important dermatologically for several reasons. First, this form removes the ionic repulsion of the two oxygen groups, thus stabilizing the molecule. Second, because the protonated form of ascorbic acid is uncharged, entry into the skin (which itself has a pH of about 3-5) should be facilitated. See H. Schaefer et al., *Skin Permeability* 739-40 (Springer-Verlag Co., Berlin, 1982).

The following examples are for illustrative purposes only and are not intended to limit the scope of the claimed invention. The spectrophotometric analyses were made on a Shimadzu UV-260 dual beam spectrophotometer under the following conditions: Samples of ascorbic acid were kept at room temperature (unless otherwise indicated), shielded from light with varying air headspace. At different times aliquots were taken from each sample and diluted into water in a quartz cuvette in the spectrophotometer "sample beam". The reference cell contained either vehicle diluted into water or water alone (no difference was detected). Spectra were then taken from 200 nm to 400 nm and the optical density at the absorption maximum (unless otherwise indicated) was used to determine concentration.

EXAMPLE I

Example I demonstrates the preparation of the claimed composition and the stability of compositions to the invention.

A concentrated solution of 0% L-ascorbic acid (w/v) is prepared by dissolving 10 g. of L-ascorbic acid (available from Sigma) in 80 ml distilled, deionized water, and adding propylene glycol (1,2 propanediol purchased from Aldrich Chemical) to 100 ml. Optionally, 1 g of hydroxypropylcellulose (average molecular weight of 300,000) may be added. For maximum stability, the solution should be stored in a light-impermeable bottle at a temperature of about $\leq 22°$ C. with minimal headspace and/or purged with nitrogen.

Figure 1:
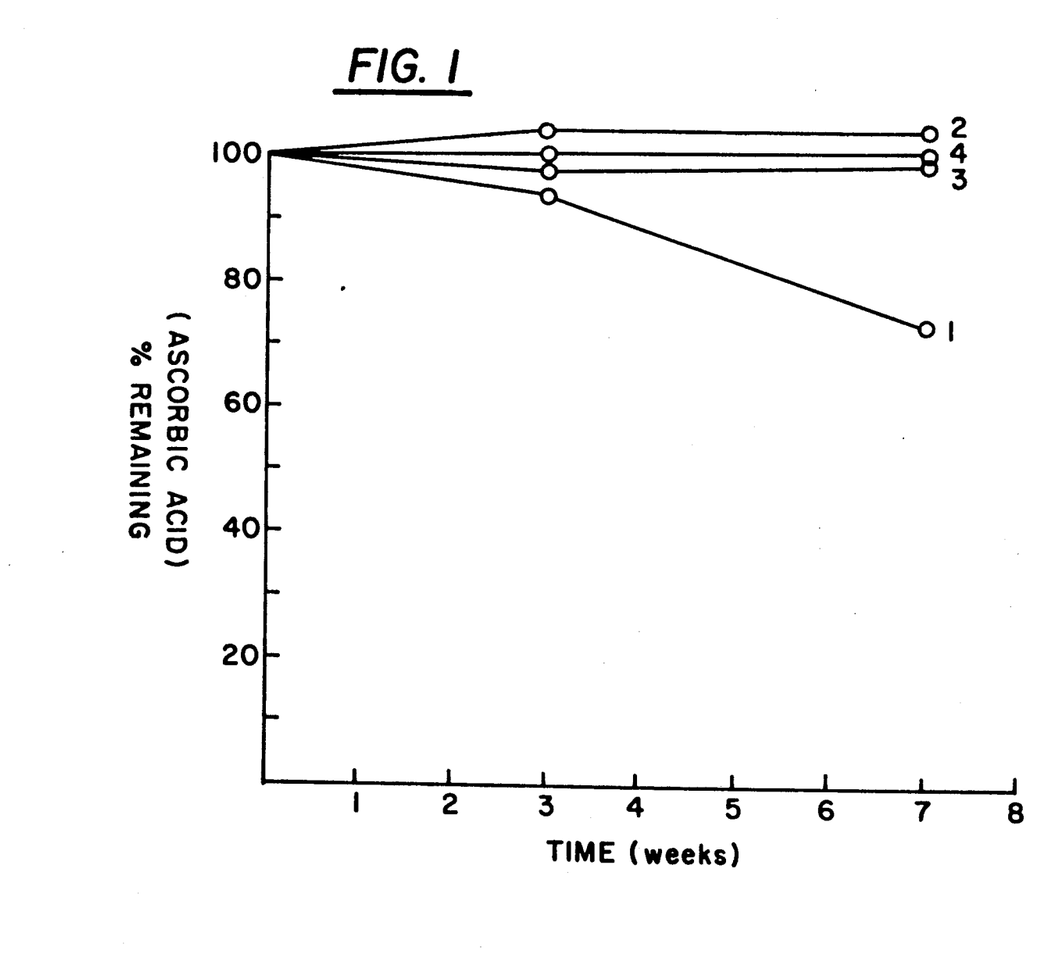

In Example I, four solutions of 10% L-ascorbic acid (w/v) in 80% $H_2O$ (v/v):20% propylene glycol (v/v):1% hydroxypropylcellulose (w/v) were prepared and kept in the dark at room temperature and capped microfuge tubes (with an approximately 10% air headspace). At indicated times, aliquots were removed and the residual ascorbic acid determined spectrophotometrically. The results are illustrated in FIG. 1.

EXAMPLE II

Figure 2:
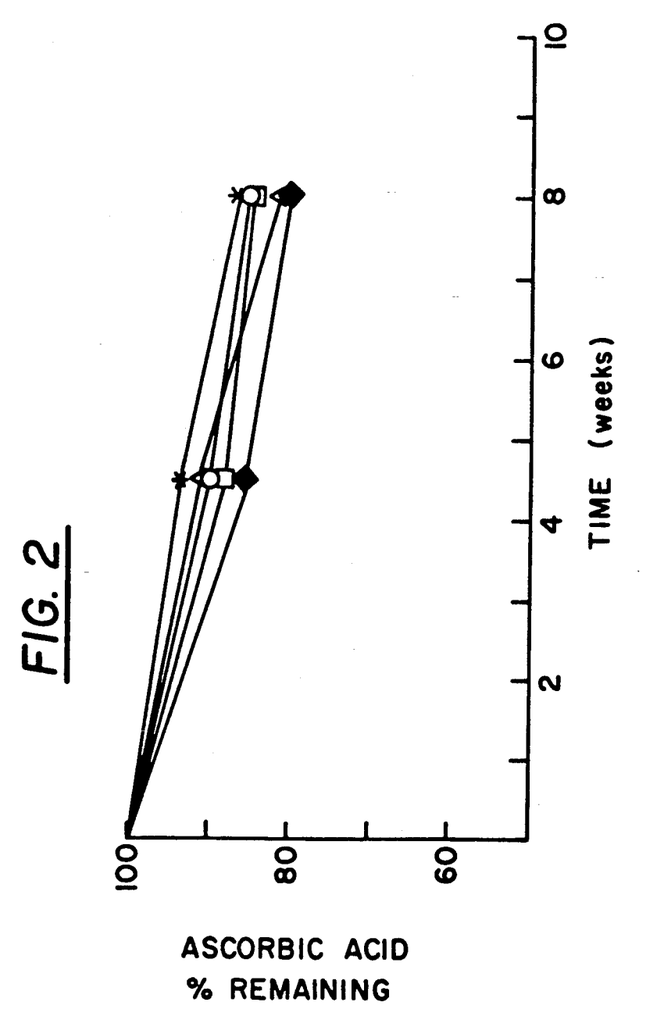
FIG. 2 shows the effect of propylene glycol concentration on the stability of L-ascorbic acid. Solutions (2% w/v) of L-ascorbic acid in water with various concentrations of propylene glycol were kept in the dark at room temperature in capped microfuge tubes (with an approximately 20% air headspace). At 4.5 and 8 weeks, aliquots were removed from each sample and the residual ascorbic acid recorded as in FIG. 1.

Example II illustrates that the stability of L-ascorbic acid is not influenced by the concentration of propylene glycol. A 2% solution of L-ascorbic acid was prepared in different concentrations of propylene glycol. These were stored in the dark, at room temperature in capped microfuge tubes with approximately 20% air headspace. At 4.5 and 8 weeks, aliquots were removed and the residual ascorbic acid determined spectrophotometrically. The results are illustrated in FIG. 2.

EXAMPLE III

Figure 3:
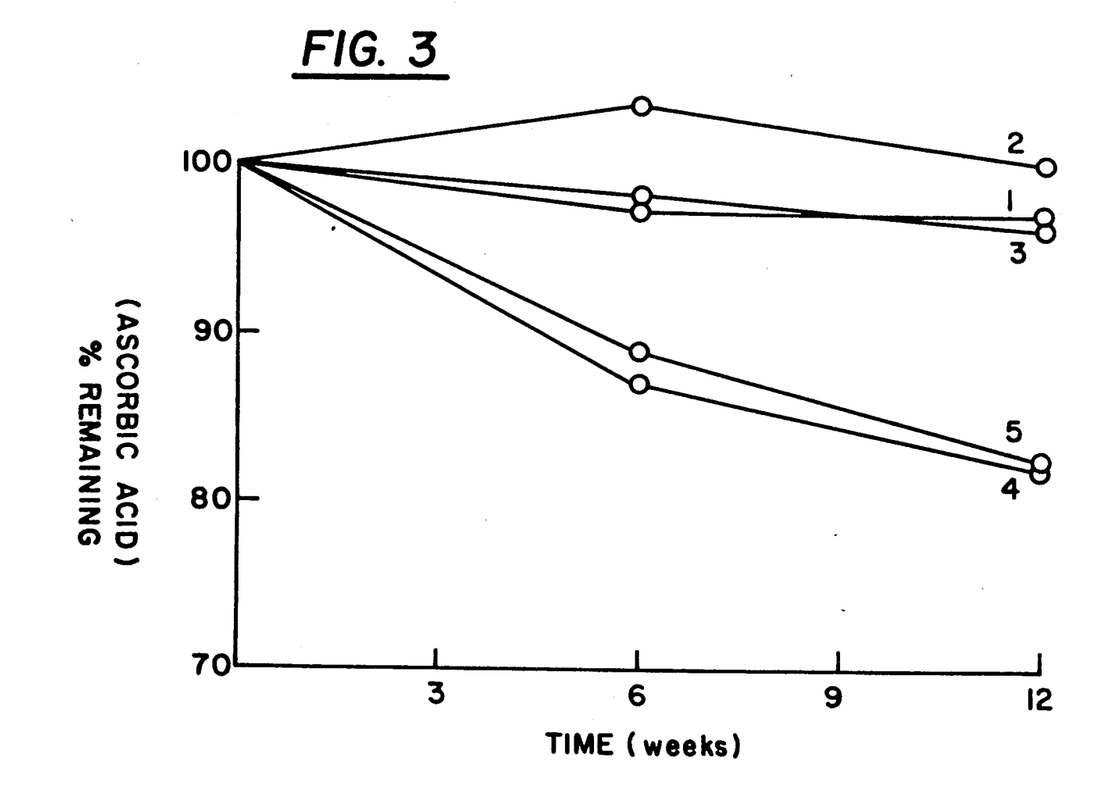

Example III illustrates the effect of pH on the stability of L-ascorbic acid in 80% $H_2O$(v/v):20% propylene glycol (v/v):1% hydroxypropylcellulose (w/v). Five percent solutions of L-ascorbic acid were adjusted to different pH's and then stored in the dark, at 4° C. in capped microfuge tubes with approximately 25% air headspace. At 6 and 12 weeks, aliquots were removed and the residual ascorbic acid determined spectrophotometrically. These results are illustrated in FIG. 3. It is apparent that even at relatively high pH's, the L-ascorbic acid at a 5% concentration is quite stable.

EXAMPLE IV

Figure 4:
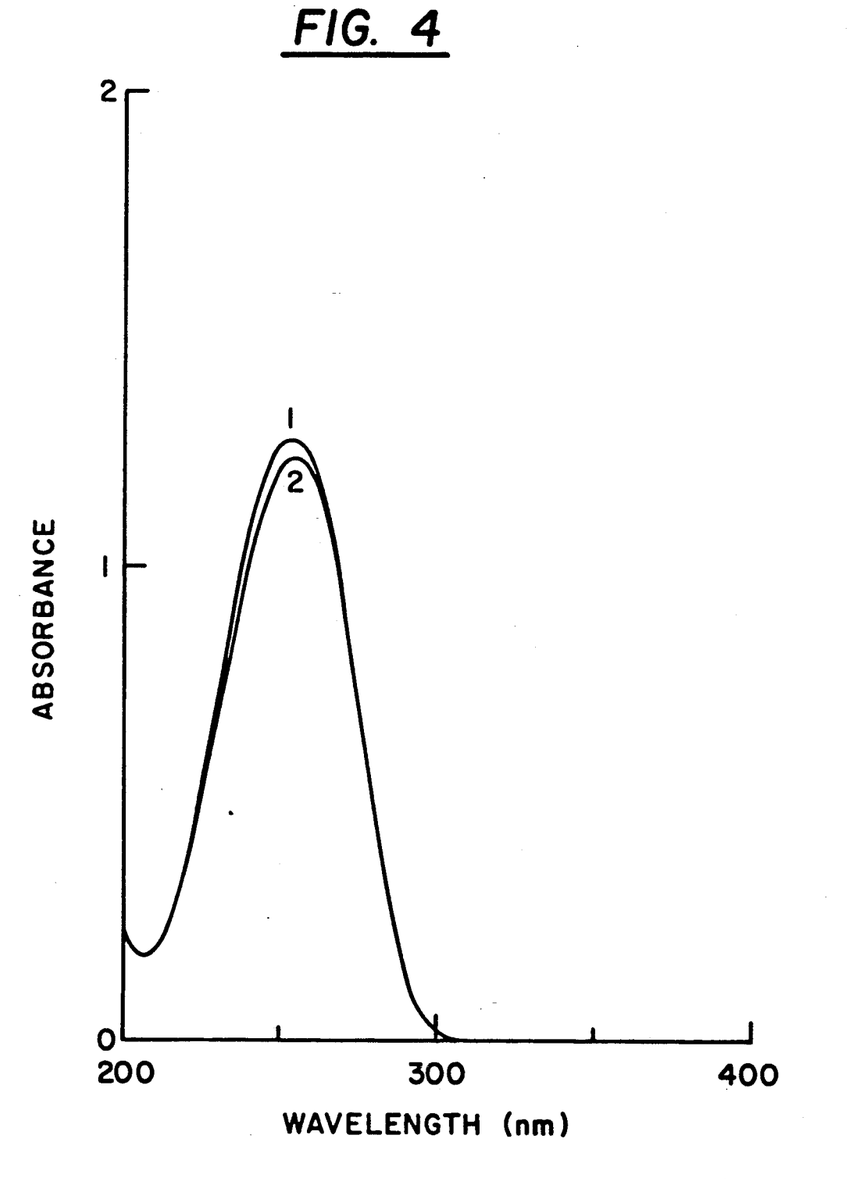
FIG. 4 shows the spectral analysis of an aqueous 5% L-ascorbic acid solution, pH 2.4. Conditions were as in FIG. 3. Spectra were taken immediately after preparation and after 12 weeks storage.
Figure 5:
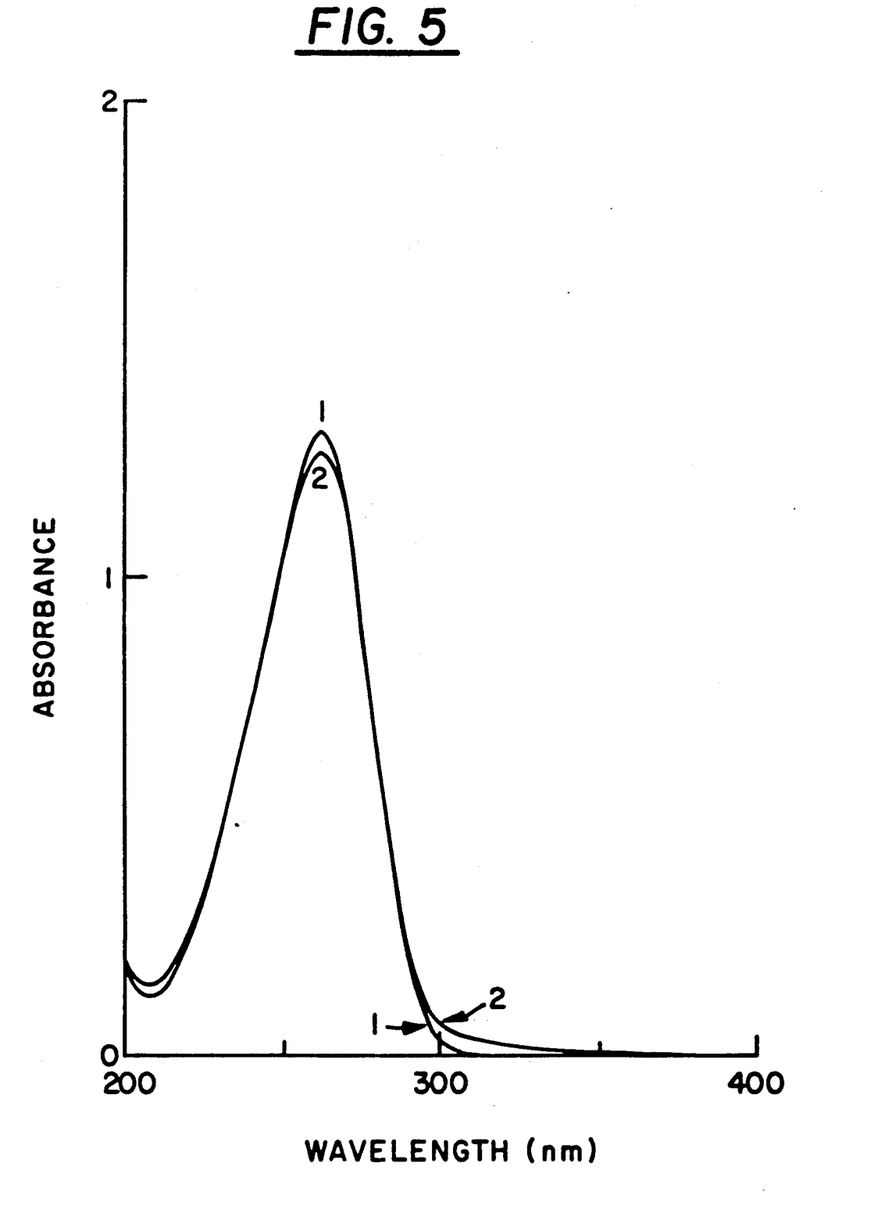
FIG. 5 shows the spectral analysis of an aqueous 5% L-ascorbic acid solution, pH 4.2. Conditions were as in FIG. 3. Spectra were taken immediately after preparation and after 12 weeks storage.

Example IV illustrates that spectral changes occur in a 5% L-ascorbic acid solution in 80% $H_2O$(v/v):20% propylene glycol(v/v):1% hydroxypropylcellulose (w/v) at relatively high pH even though the ascorbic acid is stable. From Example III, compositions at pH 2.4 and pH 4.2 were scanned either immediately after preparation or after 12 weeks storage as in Example III. The spectra are illustrated in FIGS. 4 and 5. These results indicate that reactions are occurring at pH 4.2 which lead to spectral broadening of the major peak into the near UV, as manifested by an increased "yellowing" of the solution.

EXAMPLE V

Example V illustrates that by using distilled, deionized $H_2O$ and high concentrations of ascorbic acid/ascorbate used in the formulation ($\geq 3\%$), chelators show only a slight tendency to to stabilize ascorbate. In comparison, when a 1% ascorbate solution in a propylene glycol/ethanol/$H_2O$ vehicle was made with or without oil mM DTPA, a slight protective effect of DTPA on the stability of ascorbate was found. With a 5% ascorbate solution in propylene glycol/$H_2O$ however, DTPA no longer showed any protective effect when analyzed spectrophotometrically. The data are presented in Table I. The chelator effect is expected to increase in compositions which are formulated in less pure water than those used for Example V, or those in which any of the components are contaminated with metal ions.

EXAMPLE VI

Example VI illustrates the greater stability of L-ascorbic acid compared to that of Na-ascorbate in the cosmetic preparation of 80% $H_2O$:20% propylene glycol: 1% hydroxypropylcellulose at a concentration of 1% (w/v) and 10% (w/v). At 1%, L-ascorbic acid is slightly more stable than the sodium salt, ascorbate. At 10% concentration, both L-ascorbic acid and Na-ascorbate show pronounced stability based on the spectrophotometric analyses, but the Na-ascorbate shows considerable yellow discoloration at both concentrations after 2 weeks whereas L-ascorbic acid shows only slight changes even at 7 weeks. The results are tabulated in Table II.

EXAMPLE VII

Figure 6A:
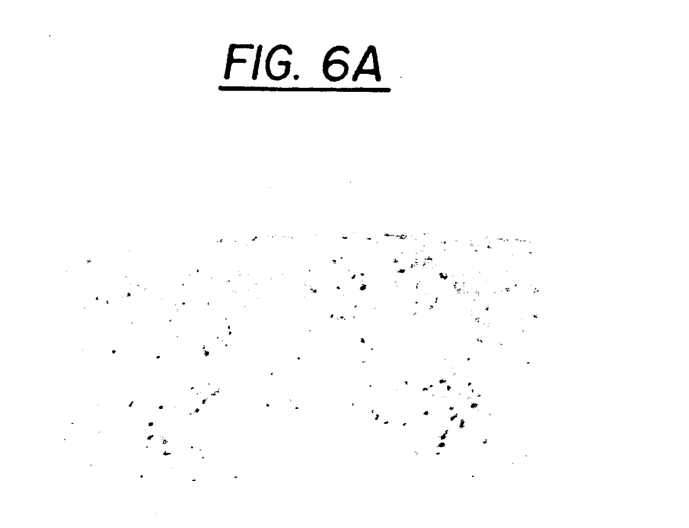
Figure 6B:
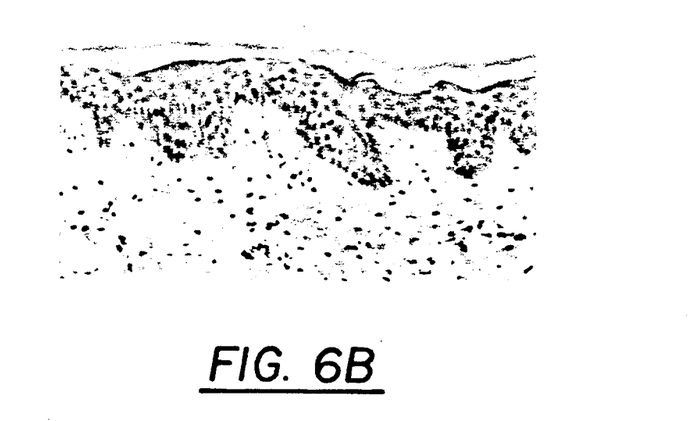

Example VII illustrates the protection of skin from ultraviolet damage by topical application of the stabilized aqueous formulation of L-ascorbic acid. In this experiment a Yorkshire swine's back was shaved with clippers and areas pretreated 8 times in 6 days with 10% solution of L-ascorbic acid in 80% $H_2O$ (v/v):20% propylene glycol (v/v):1% hydroxypropylcellulose (w/v) or the vehicle control. The back was then irradiated for 10 minutes from a distance of approximately 4 inches with a bank of two Westinghouse FS-40 sunlamps (This dose is equivalent to approximately 5 times the MED (minimal erythemal dose). The areas were post-treated twice in the ensuing 24 hours. At 24 hours, 4 mm punch biopsies were taken from each site and prepared for histology. Typical results are shown in the photomicrograph in FIG. 6 in which A = L-ascorbic acid treated; B = vehicle treated. The presence of dysplastic basal cells ("sunburn" cells) in the epidermis in response to UV is a hallmark of short wavelength UV damage to skin. The section from the L-ascorbic acid-treated site shows markedly fewer of these cells. Another difference relates to the overall stain intensity, an indication of an edematous response in skin. Quite typically, the sections from non-treated, exposed skin stain less than sections taken from ascorbic acid-treated skin, indicating a decreased edematous response in protected skin.

EXAMPLE VIII

Example VIII illustrates the reservoir effect of L-ascorbic acid protection against UV damage to the skin. Animals treated as in Example VII receive the final pretreatment 4 hours before UV exposure. In addition all treated sites are washed with luke-warm water immediately prior to irradiation eliminating any residual solution acting as a sunblock. This establishes that protection is due to L-ascorbic acid which has been taken up by the skin. This is in contrast to typical, commercially available, sunscreens which have to be applied immediately prior to exposure for optimal performance.

EXAMPLE IX

Figure 7:
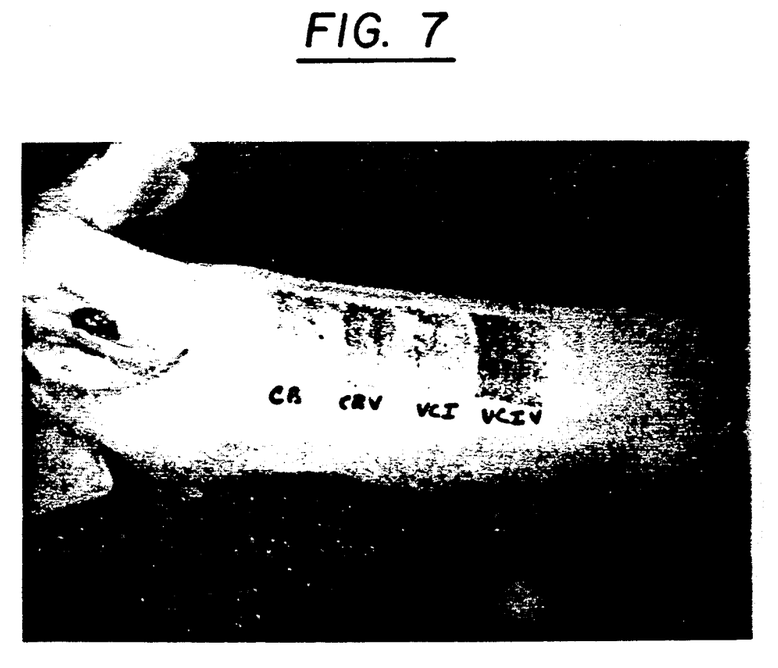
FIG. 7 shows the effect of 5% L-ascorbic acid in aqueous formulation and of 5% L-ascorbic acid in "hydroalcoholic" vehicle on acute sunburn in the domestic pig. The two ascrobic acid solutions (or their vehicle alone) were applied liberally 5 times in 6 days. On the seventh day, the animal was exposed for 60 minutes to ultraviolet irradiation (two FS-40 sunlamps at a distance of 4 inches). Photograph was taken 11 days post-irradiation. VC-I=5% L-ascorbic acid in aqueous formulation; VC-I-V=VC-I vehicle alone; CB=5L-ascorbic acid in "Hydroalcoholic vehicle"; CBV=Hydroalcoholic vehicle alone.

Example IX illustrates the potential of topical applications of L-ascorbic acid to moderate severe ultraviolet-induced skin damage. In Example IX, the test animal was pretreated with a 5% formulation of L-ascorbic acid (in either an aqueous formulation or "hydroalcoholic" vehicle) five times in six days prior to irradiation. On the sixth day, the treated and control areas were irradiated for 60 minutes with a bank of two Westinghouse FS-40 bulbs. This dose is equivalent to 30 times the minimal erythemal dose. The photograph was taken 11 days after irradiation showing the improvement in appearance of the L-ascorbic acid treated sites as compound to the control sites. The results are illustrated photographically in FIG. 7.

EXAMPLE X

Figure 8:
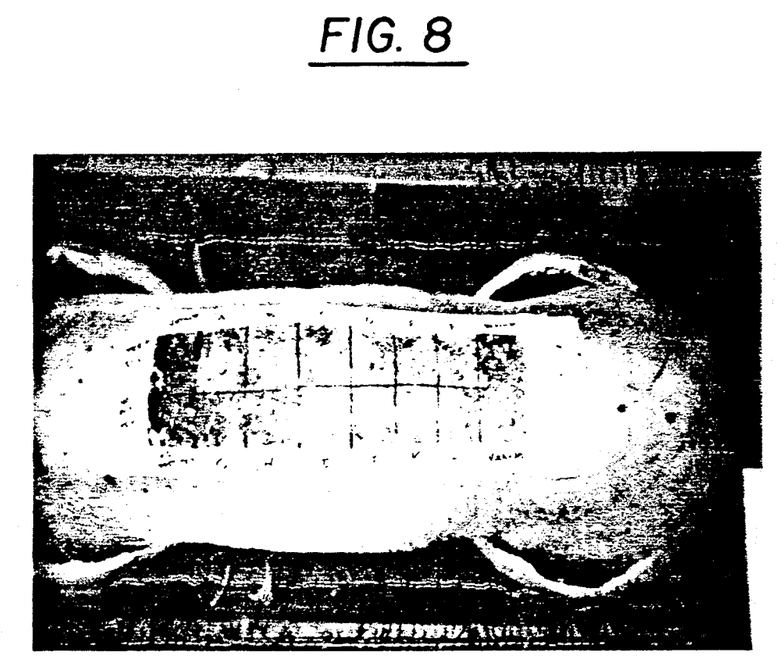
FIG. 8 shows the effect of post-exposure application of 5% L-ascorbic acid in an aqueous formulation (L-AA) on acute sunburn reaction in the pig. The top row received preexposure application of the ascorbic acid (A-F) or vehicle (vehicle) 5 times in 6 days. The bottom row received no pre-treatment. Selected sites in the top and bottom rows then received L-AA application for varying periods of time post-irradiation. A: no further application; B: L-AA, one day; C: L-AA, 2 days; D: L-AA, 3 days; E: L-AA, 5 days; F: L-AA, 7 days post-exposure; G: L-AA, 1 day; H: L-AA, 2 days; I: L-AA, 3 days; J: L-AA, 4 days; K: L-AA, 5 days; L.

Example X establishes that topical application of the aqueous L-ascorbic acid formulation has beneficial, "wound healing", effects even when applied after UV irradiation, as illustrated photographically in FIG. 8. In Example X, the test animal was pretreated and irradiated as in Example IX. One area on this animal (the bottom row in the illustration of FIG. 8) received no pretreatment. After irradiation, the sites received either no post-treatment, or post-treatment on one, two, three, four, five, or seven days with 5% L-ascorbic acid, or post-treatment with the vehicle only for seven days. With 3 to 4 days post-treatment with the L-ascorbic acid solution (I-J in FIG. 8), the appearance of skin improved as compared to those areas which were untreated or treated with vehicle only.

TOXICITY STUDIES

Although no formal toxicity studies have been conducted, a 10% solution (w/v) has been applied to the face of a human one time per day, five times per week for thirty weeks without any adverse reaction. Additionally, in preliminary studies carried out by Dr. Lorraine Kligman at the University of Pennsylvania, hairless mice were treated 5 times per week with either a 5% or 0% solution of L-ascorbic acid at either pH 2.1 or 3, or with the pH controls for 4 weeks. No evidence (clinical or histological) was found for these topical applications being either toxic or irritating.

TABLE I

Effect of a Metal Chelator on the Stability of High Concentrations of Ascorbate

| Sample | % Ascorbate remaining at | |
|---|---|---|
| | 2.5 Weeks | 3 Weeks |
| 1% Ascorbate | 31 | — |
| 1% Ascorbate + 0.1 mM DTPA | 41 | — |
| 5% Ascorbate | — | 73 |
| 5% Ascorbate + 0.1 mM DTPA | — | 73 |

1% ascorbate solutions were made in a water, propylene glycol, ethanol solution (10:60:30; v/v/v)p; 5ascorbate solutions were made in a water, propylene glycol solution (80:20; v/v) with or without the indicated amount of DPTA. The samples were kept at room temperature in capped tubes (with significant air headspace). Aliquots were initially taken daily, then weekly and measured for residual ascorbate spectrophotometrically.

TABLE II

Comparison of Stabilities of High Concentrations of L-Ascorbic Acid and Na-Ascorbate

| Sample | % Remaining at | |
|---|---|---|
| | 3 Weeks | 7 Weeks |
| 1% Na Ascorbate | 79 | 60 |
| 1% L-Ascorbic acid | 93 | 74 |
| 10% Na-Ascorbate | — | 97.5 |
| 10% L-Ascorbic Acid | — | 100 |

Ascorbic/ascorbate solutions were made in 80% H$_2$O:20% propylene glycol:1% hydroxypropylcellulose. The samples were kept in the dark at room temperature in capped microfuge tubes (with an approximately 10% air headspace). Aliquots were taken at the indicated times and measured for residual ascorbic acid/ascorbate spectrophotometrically.

BRIEF DESCRIPTION OF THE DRAWINGS

FIG. 1 shows the stability of various concentrations of L-ascorbic acid in aqueous cosmetic vehicle. Different concentrations of L-ascorbic acid were made in a vehicle composed of 80% H$_2$O, 20% propylene glycol and 1% hydroxypropylcellulose and stored shielded from light, at room temperature (with an approximately 10% air headspace). One day, 3 weeks and 7 weeks later, aliquots were diluted into a quartz cuvette and the resulting spectrum was scanned from 200 to 400 nm. The optical density of the 260-265 nm peak was recorded for lower concentrations while the optical density at 280 nm was recorded for changes in the higher concentrations of L-ascorbic acid.

1: 1% L-ascorbic acid   2: 3% L-ascorbic acid
3: 5% L-ascorbic acid   4: 10% L-ascorbic acid

O: 0% propylene glycol; □: 10% propylene glycol; Δ: 20% propylene glycol; *: 40% propylene glycol; ♦: 60% propylene glycol FIG. 3 shows the stability of a 5% aqueous solution of L-ascorbic acid at various pH's. A 5% solution of L-ascorbic acid was prepared in a vehicle of 80% H$_2$O, 20% propylene glycol and 1% hydroxypropylcellulose at the indicated pH. Samples were stored at 4 deg. C, shielded from light (from approximately 25% air headspace). After one day, six weeks and 12 weeks, aliquots were removed from each sample and the residual ascorbic acid recorded as in FIG. 1.

1: pH 2.4; 2: pH 3.2; 3: pH 4.2; 4: pH 4.5; 5: pH 5.1

FIG. 6 shows the photomicrographs of ultraviolet irradiated porcine skin treated with an aqueous L-ascrobic formulation or vehicle control. Sites on animals back were pretreated with the ascrobic acid or vehicle control eight times in the six days prior to irradiation, the last predetermined being 4 hours before irradiation. Irradiation was for 10 minutes using a bank of two Westinghous FS-40 sunlamps. Four millimeter punch biopsys were taken 24 hours later, routinely fixed and stained with (Hematoxylian and Eosin). Arrows point to sunburn cells.

L-AA, 7 days post-exposure. Vehicle sites were treated with the VC-I vehicle for the seven days post-exposure.

We claim:

1. A topical composition consisting essentially of from at least about 1% ascorbic acid (w/v) in water and a carrier suitable for topical application wherein the ratio of water to carrier is at least 1:1 and wherein the composition has a pH of no more than about 3.5.

2. The composition of claim 1 wherein the carrier comprises an alkylene glycol.

3. The composition of claim 2 wherein the alkylene glycol is propylene glycol.

4. The composition of claim 1 wherein the carrier is a combination of an alkylene glycol and hydroxyalkylcellulose.

5. The composition of claim 4 wherein the alkylene glycol is propylene glycol.

6. The composition of claim 1 wherein the ratio of water to carrier is from about 2:1 to about 10:1.

7. The composition of claim 2 wherein the ratio of water to carrier is from about 2:1 to about 10:1.

8. The composition of claim 3 wherein the ratio of water to carrier is from about 2:1 to about 10:1.

9. A topical composition consisting essentially of between 3 and 20% ascorbic acid (w/v) and 80% to 97% water and a carrier suitable for topical application wherein the ratio of water to carrier is at lest about 1:1 and wherein the composition has a pH of no more than about 3.5.

10. The composition of claim 9 wherein the carrier is a combination of an alkylene glycol and hydroxyalkylcellulose.

11. The composition of claim 10 wherein the ratio of alkylene glycol to hydroxyalkylcellulose is from about 30:1 to 5:1.

12. The composition of claim 11 wherien the alkylene glycol is propylene glycol and the hydroxylalkycellulose is hydroxypropylcellulose.

13. The composition of claim 1 or 9 wherein the composition is a dermatogical composition and the carrier is a dermatological carrier.

14. The composition of claim 1 or 9 wherein the pH is no more than about 2.5.

15. The composition of claim 1 wherein the water is selected from the group consisting of distilled, deionized and distilled deionized water.

16. The composition of claim 15 wherien the pH is no more than about 2.5.

17. A topical composition consisting essentially of about 5 to 10% ascorbic acid (w/v) and about 90 to 95% water and a carrier suitable for topical application wherein the ratio of water to carrier is at least about 1:1 and wherein the composition has a pH of no more than about 3.5.

18. The composition of claim 17 wherein the carrier is a combination of an alkylene glycol and hydroxyalkycellulose.

19. The composition of claim 18 wherein the ratio of alkylene glycol to hydroxyalkylcellulose is from about 30:1 to 5:1.

20. The composition of claim 19 wherein the alkylene glycol is propylene glycol and the hydroxyalkylcellulose is hydroxypropycellulose.

21. The composition of claim 17 wherein the water is distilled, deionized, or distilled deionized water.

22. A topical composition containing from at least about 1% ascorbic acid (w/v) in water and a carrier suitable for topical application wherein the ratio of water to carrier is at least 1:1 and wherein the composition has a pH of no more than about 3.5.

23. The composition of claim 22 wherein the cosmetic carrier comprises an alkylene glycol.

24. The composition of claim 23 wherein the pH is no more than about 2.5.

25. The composition of claim 22 wherein the water is selected from the group consisting of distilled, deionized and distilled deionized water.

26. The composition of claim 25 wherein the Ph is no more than about 2.5.

27. The composition of claim 22 wherein the composition is a dermatoligical composition and the carrier is a dermatological carrier.

28. The composition of claim 23 wherein the ratio of water to carrier is from about 2:1 to about 10:1.

29. A topical composition containing between 3 20% ascorbic acid (w/v) and 80% to 97% water and a carrier suitable for topical application wherein the ratio of water to carrier is at least about 1:1 and wherein the composition has a pH of no more than about 3.5.

30. The composition of claim 29 wherein the carrier is a combination of an alkylene glycol and hydroxyalkylcellulose.

31. A topical composition containing about 5 to 10% ascorbic acid (w/v) and about 90 to 95% water and a carrier suitable for topical application wherein the ratio of water to carrier is at least about 1:1 and wherein the composition has a pH of no more than about 3.5.

32. A method of retarding damage to skin by ultraviolet light which comprises applying a topical composition on the skin consisting essentially of at least about 1% ascorbic acid (w/v) in water and a carrier suitable for topical application wherein the ratio of water to carrier is at least about 1: 1 and wherein composition has a pH of mo more than about 3.5.

33. The method of claim 32 wherein the topical composition consists essentially of between about 3 and 20% ascorbic acid (w/v) and 80 to 97% water and carrier (v/v).

34. The method of claim 33 wherein the carrier comprises an alkylene glycol and hydroxyalkylcellulose.

35. The method of claim 34 wherein the alkylene glycol is propylene glycol and the hydroxyalkylcellulose is hydroxypropylcellulose.

36. The method of claim 34 wherein the ratio of water to carrier is from about 2: 1 to about 10:1.

37. The method of claim 35 wherein the ratio of water to carrier is from about 2:1 to about 10:1.

38. A method of preventing damage to skin by ultraviolet light comprising the step of applying a topical composition to the skin consisting essentially of from at least about 1% ascorbic acid (w/v) in water and a carrier suitable for topical application wherein the ratio of water to carrier is at least 1:1 and wherein the composition has a pH of no more than about 3.5.

39. The method of claim 38 wherein the topically applied composition consists essentially of between 3 and 20% ascorbic acid (w/v) and 80% to 97% water and a carrier suitable for topical application wherein the ratio of water to carrier is at least about 1:1 and wherein the composition has a pH of no more than about 3.5.

40. A method of treating damage to skin by ultraviolet light comprising the step of applying a topical composition to the skin consisting essentially of from at least about 1% ascorbic acid (w/v) in water and a carrier suitable for topical application wherein the ratio of water to carrier is at least 1:1 and wherein the composition has a pH of no more than about 3.5.

41. The method of claim 40 wherein the topically applied composition consists essentially of between 3 and 20% ascorbic acid (w/v) and 80% to 97% water and a carrier suitable for topical application wherein the ratio of water to carrier is at least about 1:1 and wherein the composition has a pH of no more than about 3.5.

42. A method of retarding damage to skin by ultraviolet light which comprises applying a topical composition to the skin containing at least about 1% ascorbic acid (w/v) in water and a carrier suitable for topical application wherein the ratio of water to carrier is at least about 1:1 and wherein composition has a pH of no more than about 3.5.

* * * * *